US012682585B2

(12) United States Patent
Lee

(10) Patent No.: US 12,682,585 B2
(45) Date of Patent: Jul. 14, 2026

(54) DATA PROCESSING DEVICE AND DATA PROCESSING METHOD

(71) Applicant: MEDIT CORP., Seoul (KR)

(72) Inventor: Dong Hoon Lee, Seoul (KR)

(73) Assignee: MEDIT CORP., Seoul (KR)

( * ) Notice: Subject to any disclaimer, the term of this patent is extended or adjusted under 35 U.S.C. 154(b) by 170 days.

(21) Appl. No.: 18/034,966

(22) PCT Filed: Nov. 3, 2021

(86) PCT No.: PCT/KR2021/015801
§ 371 (c)(1),
(2) Date: May 2, 2023

(87) PCT Pub. No.: WO2022/098087
PCT Pub. Date: May 12, 2022

(65) Prior Publication Data
US 2023/0401804 A1     Dec. 14, 2023

(30) Foreign Application Priority Data

Nov. 3, 2020     (KR) ........................ 10-2020-0145535
Sep. 28, 2021     (KR) ........................ 10-2021-0128340

(51) Int. Cl.
*G06T 19/20*          (2011.01)
*A61C 9/00*           (2006.01)
(Continued)

(52) U.S. Cl.
CPC ............ *G06T 19/20* (2013.01); *A61C 9/0053* (2013.01); *A61C 13/34* (2013.01); *G06V 10/82* (2022.01);
(Continued)

(58) Field of Classification Search
None
See application file for complete search history.

(56) References Cited

U.S. PATENT DOCUMENTS

2014/0379356 A1* 12/2014 Sachdeva ............... A61C 7/002
                                                              705/2
2019/0014970 A1*  1/2019 Clausen ........... A61B 1/000095
                        (Continued)

FOREIGN PATENT DOCUMENTS

KR          10-1769334 B1      8/2017
KR      10-2017-0142572 A     12/2017
                        (Continued)

OTHER PUBLICATIONS

Zhu et al. (UGAN: Untraceable GAN for Multi-Domain Face Translation, Computer Vision and Pattern Recognition, 2019) (Year: 2019).*

(Continued)

*Primary Examiner* — Kyle Zhai

(74) *Attorney, Agent, or Firm* — Sughrue Mion, PLLC

(57)          ABSTRACT

Provided is an oral image processing method including obtaining, as a first image, a face image of an object showing a teeth area, obtaining a second image by replacing the teeth area included in the first image with a virtual teeth area, and obtaining, from the second image, a third image including a face having a different attribute from a face included in the second image, by using a neural network trained to generate, from an input face image, a face image having a different attribute from the input face image.

7 Claims, 11 Drawing Sheets

(51) Int. Cl.

| | |
|---|---|
| *A61C 13/34* | (2006.01) |
| *G06V 10/82* | (2022.01) |
| *G06V 10/94* | (2022.01) |
| *G06V 40/16* | (2022.01) |
| *G16H 30/40* | (2018.01) |

(52) U.S. Cl.
CPC .......... *G06V 10/945* (2022.01); *G06V 40/171* (2022.01); *G16H 30/40* (2018.01); *G06T 2200/24* (2013.01); *G06T 2210/41* (2013.01); *G06T 2219/2004* (2013.01); *G06T 2219/2024* (2013.01); *G06V 2201/03* (2022.01)

(56) References Cited

U.S. PATENT DOCUMENTS

| | | | | |
|---|---|---|---|---|
| 2019/0357997 | A1* | 11/2019 | Shi ........................ | G06V 40/171 |
| 2020/0066391 | A1* | 2/2020 | Sachdeva ............... | G16H 20/40 |
| 2020/0081413 | A1* | 3/2020 | Georg .................... | G06F 30/20 |
| 2020/0105028 | A1 | 4/2020 | Gao et al. | |

FOREIGN PATENT DOCUMENTS

| | | |
|---|---|---|
| KR | 10-2019-0092699 A | 8/2019 |
| KR | 10-2020-0026808 A | 3/2020 |
| WO | 2016/003257 A2 | 1/2016 |
| WO | 2019/014646 A1 | 1/2019 |

OTHER PUBLICATIONS

Coachman et al. (Dynamic Documentation of the Smile and the 2D/3D Digital Smile Design Process, Int J Periodontics Restorative Dent, 2017) (Year: 2017).*

Aleksandr Amirkhanov, et al., "*WithTeeth*: Denture Preview in Augmented Reality", Vision, Modeling, and Visualization, 2018, XP055574940, 10 pages.

Yurika Sagawa, et al., "Face Image Generation System Using Attribute Information with DCGANs", Machine Learning and Soft Computing, Feb. 2, 2018, XP058397, pp. 109-113.

Communication dated Sep. 16, 2024 issued by the European Patent Office in application No. 21889552.2.

Woong Been Son, "A Study of Soft Tissue Predication of Lateral Facial Profile after Orthognathic Surgery using Artificial Neural Networks.", Department of Dentistry, School of Dentistry, Seoul National University, May 29, 2018, pp. 1-31.

International Search Report for PCT/KR2021/015801 dated Feb. 3, 2022 [PCT/ISA/210].

Office Action issued May 23, 2024 in Korean Application No. 10-2021-0128340.

Yunjey Choi, et al., "StarGAN: Unified Generative Adversarial Networks for Multi-Domain Image-to-Image Translation", arXiv:1711.09020v3, Sep. 21, 2018, pp. 1-15.

* cited by examiner

DATA PROCESSING DEVICE AND DATA PROCESSING METHOD

TECHNICAL FIELD

Embodiments relate to a data processing device and a data processing method, and more particularly, to an apparatus and method for processing an oral image.

BACKGROUND ART

A 3-dimensional (3D) scanner is used for dental treatment of patients. The 3D scanner may be a handheld type capable of being placed into or taken out of the mouth of a patient or in a table scanner form capable of scanning a plaster model arranged on a table by using rotation of the table.

A data processing device, such as a personal computer (PC), connected to the 3D scanner may generate a 3D oral image by using raw data obtained by the 3D scanner.

A user, such as a dentist or the like, may perform dental treatment, such as prosthetic treatment or orthodontic treatment, on the oral cavity of a patient. Such dental treatment may include various types of aesthetic treatments.

The patient may want to previously know a state of his/her oral cavity when the dental treatment is completed. Also, the patient may want to know how his/her oral cavity after treatment will look on the face. In this regard, a technology of simulating how a virtual oral cavity after treatment will look on the face of the patient having various facial expressions or poses, and providing simulation results to the patient is required.

DISCLOSURE

Technical Solution

Ann oral image processing method according to an embodiment includes obtaining, as a first image, a face image of an object showing a teeth area, obtaining a second image by replacing the teeth area included in the first image with a virtual teeth area, and obtaining, from the second image, a third image including a face having a different attribute from a face included in the second image, by using a neural network trained to generate, from an input face image, a face image having a different attribute from the input face image.

DESCRIPTION OF DRAWINGS

FIG. 8 is a diagram for describing face images having different attributes being obtained from a face image input through a neural network, according to an embodiment.

MODE FOR INVENTION

Figure 1:
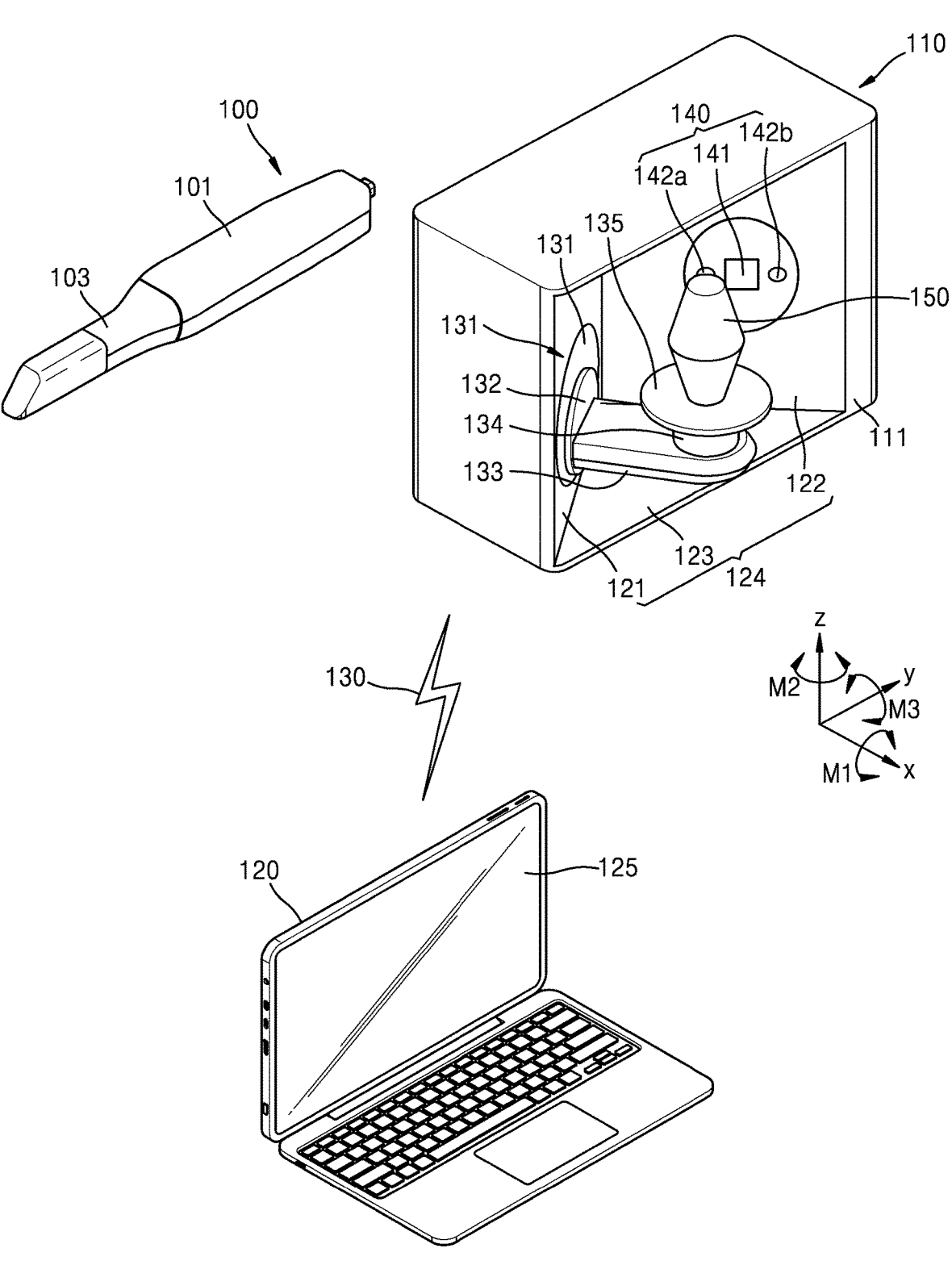
FIG. 1 is a diagram for describing an oral image processing system according to an embodiment.

According to an embodiment, the face having the different attribute from the face included in the second image may be a face different from the face included in the second image in at least one of a pose, a facial expression, a degree the teeth area is shown, and a style.

According to an embodiment, the neural network may be a deep neural network (DNN) for obtaining a face image from a multi-domain by converting an attribute of the input face image, wherein the DNN may include a star generative adversarial network (StarGAN).

According to an embodiment, the oral image processing method may further include obtaining a 3-dimensional (3D) oral model by scanning an oral cavity of the object, obtaining a target virtual oral model from the 3D oral model, and obtaining, as the virtual teeth area, an area corresponding to the teeth area included in the first image, from the virtual oral model.

According to an embodiment, the 3D oral model may include 3D scan data of at least one of an upper jaw, a lower jaw, and occlusion from among the oral of the object.

According to an embodiment, the obtaining of the second image may include detecting a lip line included in the face image of the object included in the first image, wherein the teeth area may include an internal area of the detected lip line, and the virtual teeth area may include an area corresponding to the internal area of the detected lip line from the virtual oral model.

According to an embodiment, the obtaining of the second image may include obtaining a first feature point from the teeth area included in the first image, obtaining a second feature point from the virtual oral model, and aligning the first feature point and the second feature point.

According to an embodiment, the obtaining of the second image may further include receiving, from a user, selection on the first feature point and the second feature point from each of the teeth area and the virtual oral model.

According to an embodiment, the oral image processing method may further include obtaining, as an additional image, a face image of the object, which includes a greater teeth area than the first image, wherein the obtaining of the second image may include replacing the greater teeth area included in the additional image with a virtual teeth template, obtaining, as the virtual teeth area, an area corresponding to the teeth area included in the first image from the greater teeth area replaced with the virtual teeth template, and obtaining the second image by replacing the teeth area included in the first image with the virtual teeth area.

An oral image processing apparatus according to an embodiment includes a processor configured to execute at least one instruction, wherein the processor is configured to execute the at least one instruction to obtain, as a first image, a face image of an object showing a teeth area, obtain a second image by replacing the teeth area included in the first image with a virtual teeth area, and obtain, from the second image, a third image including a face having a different attribute from a face included in the second image, by using a neural network trained to generate, from an input face image, a face image having a different attribute from the input face image.

A computer-readable recording medium according to an embodiment has recorded thereon a program for implementing an oral image processing method including obtaining, as a first image, a face image of an object showing a teeth area, obtaining a second image by replacing the teeth area included in the first image with a virtual teeth area, and obtaining, from the second image, a third image including a face having a different attribute from a face included in the second image, by using a neural network trained to generate, from an input face image, a face image having a different attribute from the input face image.

The present specification describes the principles of the present application and discloses embodiments such that the scope of right of the present application is clarified and one of ordinary skill in the art may practice the present application. The embodiments may be implemented in various forms.

Throughout the specification, like reference numerals denote like elements. The present specification does not describe all elements of the embodiments, and generic content in the technical field of the present application or redundant content of the embodiments is omitted. The term "part" or "portion" used in the specification may be implemented by software or hardware, and according to embodiments, a plurality of "parts" or "portions" may be implemented as one unit or element, or alternatively, one "part" or "portion" may include a plurality of units or elements. Hereinafter, operation principles and embodiments of the present application will be described with reference to accompanying drawings.

In the present specification, an image may include an image (hereinafter, referred to as an "oral image") indicating at least one tooth, an oral cavity including at least one tooth, or a plaster model of an oral cavity.

Also, in the present specification, an image may include a 2-dimensional (2D) image of an object or a 3D oral image stereoscopically indicating an object. The 3D oral image may also be referred to as a 3D oral model because the 3D oral image may be generated by 3-dimensionally modeling a structure of an oral cavity, based on raw data. The 3D oral model may also be referred to as 3D scan model or 3D scan data.

Hereinafter, in the present specification, an oral image will be used as a general term for a model or image representing an oral cavity 2-dimensionally or 3-dimensionally.

Also, in the present specification, data may denote information required to represent an object 2-dimensionally or 3-dimensionally, for example, raw data obtained by using at least one camera.

In detail, the raw data is data obtained to generate the oral image, and may be data (hereinafter, referred to as 2D data) obtained by at least one image sensor included in a 3D scanner when the object is canned by using the 3D scanner. The raw data obtained by the 3D scanner may be referred to as 2D image data. The raw data may denote 2D images in different viewpoints, which are obtained by a plurality of cameras when the object is scanned by using the 3D scanner.

Hereinabove, it is described that the raw data is a 2D image, but the raw data is not limited thereto, and may be 3D image data.

In the present specification, the object may be a target to be photographed, and may be a part of a body or include a model of a part of a body. The object may include an oral cavity, a plaster model or impression model of an oral cavity, an artificial structure insertable into an oral cavity, or a plaster model or impression model of the artificial structure. For example, the object may be teeth or gums, a plaster model or impression model of teeth or gums, an artificial structure insertable into an oral cavity, or a plaster model or impression model of the artificial structure. Here, the artificial structure insertable into an oral cavity may include at least one of, for example, an orthodontic appliance, an implant, a crown, an inlay, an onlay, an artificial tooth, and an orthodontic aid inserted into an oral cavity. The orthodontic appliance may include at least one of a bracket, an attachment, an orthodontic screw, a lingual orthodontic appliance, and a removable orthodontic retainer.

A patient may receive dental treatment, such as prosthetic treatment or orthodontic treatment for the oral cavity. The dental treatment may include various types of treatments, for example, correcting an occlusion position of an upper jaw and a lower jaw when an occlusion state of upper and lower teeth is not normal, correcting an arrangement position of teeth arranged non-aesthetically, correcting a color tone or the like of a discolored tooth, implanting an artificial tooth, such as an implant, into a missing part or a part where a tooth is extracted, and performing laminate treatment. Through such dental treatment, an oral region may be more aesthetically shown than before treatment.

The patient may want to check in advance how his/her oral cavity, i.e., a virtual oral cavity, looks like on the face when oral treatment is done. The patient may want to know how the virtual oral cavity looks like not only in one face image, but also in face images of various attributes. For example, the patient may want to check how the teeth after treatment looks like on various faces, when his/her face poses variously or makes various facial expressions, or when the degree of teeth shown on the face varies. In this regard, a technology for combining a virtual oral image with the face of the patient in various situations and providing results thereof is required.

Embodiments come from recognizing the necessity of such a technology, and provide a method and apparatus for replacing a teeth area with a virtual teeth area from a face image of a patient and obtaining face images having a plurality of attributes from the face image of the patient replaced with the virtual teeth area, through a neural network.

Hereinafter, embodiments will be described in detail with reference to accompanying drawings.

FIG. 1 is a diagram for describing an oral image processing system according to an embodiment.

Referring to FIG. 1, the oral image processing system may include a 3D scanner 100 and 110, and a data processing device 120 connected to the 3D scanner 100 and 110 through a communication network 130.

The 3D scanner 100 and 110 may be a medical device obtaining an image of an object.

The 3D scanner 100 and 110 may obtain an image of at least one of an oral cavity, an artificial structure, and a plaster model of the oral cavity or artificial structure.

The 3D scanner 100 and 110 may include at least one of an oral scanner 100 and a table scanner 110.

According to an embodiment, the 3D scanner 100 and 110 may include the oral scanner 100. The oral scanner 100 may be a handheld type for scanning an oral cavity while a user holds it with a hand, and moves the oral scanner 100. The oral scanner 100 may obtain an image of an oral cavity including at least one tooth by being inserted into the oral cavity and scanning the at least one tooth in a non-contact manner.

The oral scanner 100 may include a body 101 and a tip 103. The body 101 may include a light projector (not shown) projecting light, and a camera (not shown) obtaining the image by photographing the object.

The tip 103 is a portion inserted into the oral cavity and may be detachably mounted on the body 101. The tip 103 may include a light path changer to direct the light projected from the body 101 to face the object and direct light received from the object to face the body 101.

The oral scanner 100 may obtain, as raw data, surface information of the object so as to obtain an image of at least one surface from among a tooth, a gum, and an artificial structure (e.g., an orthodontic appliance including a bracket and a wire, an implant, an artificial tooth, or an orthodontic aid inserted into an oral cavity) insertable into the oral cavity.

According to an embodiment, the 3D scanner 100 and 110 may include the table scanner 110. The table scanner 110 may be a scanner obtaining, as raw data, surface information about an object 150 by scanning the object 150 by using rotation of a table 135. The table scanner 110 may scan a surface of the object 150, such as a plaster model or impression model of an oral cavity, an artificial structure insertable into an oral cavity, or a plaster model or impression model of the artificial structure.

The table scanner 110 may include an internal space 124 provided by being dented in an inner direction of a housing 111. The internal space 124 may be formed by a first inner surface 121, a second inner surface 122, a third inner surface 123 (a bottom surface), and a fourth inner surface (not shown) (a ceiling surface).

The object 150 may be placed in the internal space 124 and the internal space 124 may include a moving portion 131 capable of moving the object 150. The moving portion 131 may move in an up-and-down direction along a z-axis direction. The moving portion 131 may include a fixed base 131 fixed on the first inner surface 121 and connected to a first rotating portion 132, the first rotating portion 132 rotatable in a first rotating direction M1 based on one point on the fixed base 131 as a center axis, for example, an x-axis as the center axis, and a beam portion 133 connected to and protruding from the first rotating portion 132. The beam portion 133 may extend or be shortened in an x-axis direction.

A second rotating portion 134 having a cylindrical shape and rotatable in a second rotating direction M2 using a z-axis as a rotating axis may be connected to the other end of the beam portion 133. The table 135 rotating together with the second rotating portion 134 may be provided on one surface of the second rotating portion 134.

An optical unit 140 may be provided on the second inner surface 122 on the internal space 124 of the housing 111. The optical unit 140 may include a light projector 141 projecting pattern light to the object 150, and at least one of cameras 142a and 142b obtaining a plurality of 2D frames by using light reflected from the object 150. The optical unit 140 may further include a second rotating portion (not shown) rotating using the center of the light projector 141 as a rotating axis while being combined to the second inner surface 122. The second rotating portion may rotate the light projector 141, the first camera 142a, and the second camera 142b in a third rotating direction M3.

The 3D scanner 100 and 110 may transmit the obtained raw data to the data processing device 120 through the communication network 130.

The data processing device 120 may be connected to the 3D scanner 100 and 110 through the communication network 130 wirelessly or via wires. The data processing device 120 may be any electronic device capable of receiving the raw data from the 3D scanner 100 and 110, and generating, processing, displaying, and/or transmitting an oral image, based on the received raw data. For example, the data processing device 120 may be a computing device, such as a smartphone, a laptop computer, a desktop computer, a personal digital assistant (PDA), or a tablet personal computer (PC), but is not limited thereto. Also, the data processing device 120 may be present in the form of a server (or a server device) for processing the oral image.

The data processing device 120 may generate a 3D oral image by processing 2D image data or generate additional information, based on the 2D image data received from the 3D scanner 100 and 110. The data processing device 120 may display the 3D oral image and/or the additional information through a display 125, or output or transmit the same to an external device.

As another example, the 3D scanner 100 and 110 may obtain the raw data through an oral scan, generate 3D data by processing the obtained raw data, and transmit the 3D data to the data processing device 120. In this case, the data processing device 120 may receive a 3D oral model from the 3D scanner 100 and 110. Alternatively, the data processing device 120 may receive a 3D oral image from an external server or external device through a wired or wireless communication network.

According to an embodiment, the data processing device 120 may obtain, as a first image, a face image of an object showing a teeth area. The data processing device 120 may obtain a second image by replacing the teeth area included in the first image with a virtual teeth area. The data processing device 120 may obtain, from the second image, a third image including a face having a different attribute from a face included in the second image, by using a neural network trained to generate, from an input face image, a face image having a different attribute from the input face image. The data processing device 120 may display the obtained third image through the display 125, or transmit or output the same to an external device.

According to an embodiment, the 3D scanner 100 and 110 may obtain the 3D data of the object by using various methods. For example, the 3D scanner 100 and 110 may obtain the 3D data of the object by using a confocal method. The confocal method is a method of obtaining 3D information of the object, based on a location of a point determined through maximum intensity of reflected light, according to a refractive index of a lens transmitting light projected onto the object. The 3D scanner 100 and 110 may obtain an optical sectional image having high spatial resolution, by using a pinhole structure. The 3D scanner 100 and 110 may obtain the 3D data by stacking 2D images obtained along an axis direction.

Alternatively, according to an embodiment, the 3D scanner 100 and 110 may obtain the 3D information of the object by using a triangulation technique. The triangulation technique is a technique for obtaining the 3D information of the object through triangulation by using a triangle formed by a light source, an object onto which light projected from the light source is projected, and an image sensor into which light reflected from the object is input. The 3D scanner 100 and 110 may obtain the 3D data indicating a shape of the object by using the principle of triangulation according to a change in a pattern, by projecting pattern light onto the object and scanning the object onto which the pattern light is projected.

This is only an embodiment, and the 3D scanner 100 and 110 may obtain the 3D data via various methods in addition to the confocal method and the triangulation technique, and transmit the 3D data to the data processing device 120. The data processing device 120 may analyze, process, display, and/or transmit the received 3D data.

Figure 2:
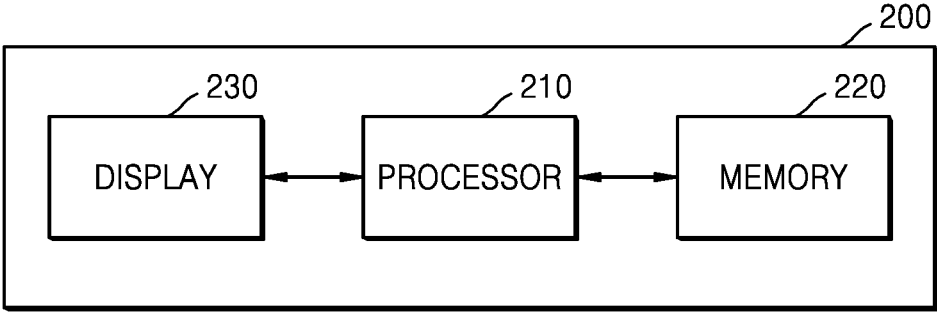
FIG. 2 is an internal block diagram of a data processing device according to an embodiment.

FIG. 2 is an internal block diagram of a data processing device according to an embodiment.

According to an embodiment, a data processing device 200 may also be referred to as an oral image processing apparatus.

The data processing device 200 of FIG. 2 may be an embodiment of the data processing device 120 of FIG. 1. Accordingly, details overlapping those described with reference to the data processing device 120 of FIG. 1 will be omitted.

The data processing device 200 may be an electronic device capable of generating, processing, displaying, and/or transmitting an oral image, by using raw data received from the 3D scanner 100 and 110.

Referring to FIG. 2, the data processing device 200 may include a processor 210, a memory 220, and a display 230.

The data processing device 200 may generate a 3D oral model, based on the raw data received from the 3D scanner 100 and 110. Alternatively, the data processing device 200 may receive the 3D oral model from the 3D scanner 100 and 110. Alternatively, the data processing device 200 may receive the 3D oral image from an external server or external device through a wired or wireless communication network.

The memory 220 according to an embodiment may store at least one instruction. The memory 220 may store at least one instruction or program executed by the processor 210. The memory 220 may store data received from the 3D scanner 100 and 110, for example, raw data obtained by scanning an oral cavity or an oral model. Also, the memory 220 may store a 3D oral image generated by the data processing device 200, received from the 3D scanner 100 and 110, or received from an external server or an external device.

According to an embodiment, the memory 220 may store an image including a teeth area. According to an embodiment, the memory 220 may store a face image of an object including the teeth area.

According to an embodiment, the memory 220 may store one or more instructions for identifying a teeth area from a face image.

According to an embodiment, the memory 220 may store one or more instructions for replacing a teeth area with a virtual teeth area.

According to an embodiment, the memory 220 may store dedicated software for replacing a 3D oral model with a target virtual oral model.

According to an embodiment, the memory 220 may store dedicated software for replacing a teeth area included in a 2D face image of an object showing teeth with a virtual teeth template.

According to an embodiment, the memory 220 may store dedicated software for detecting a teeth area from an image and replacing the teeth area with a virtual teeth area. The dedicated software for replacing a teeth area with a virtual teeth area may also be referred to as a dedicated program, a dedicated tool, or a dedicated application.

According to an embodiment, the memory 220 may include a neural network trained to generate a face image having a different attribute from an input face image, from the input face image.

The processor 210 according to an embodiment may control overall operations of the data processing device 200. The processor 210 performs at least one instruction to control an intended operation to be performed. Here, the at least one instruction may be stored in the memory 220 included in the data processing device 200 separately from the processor 210, or may be stored in an internal memory (not shown) included in the processor 210.

In detail, the processor 210 may perform the at least one instruction to control at least one component included in the data processing device 200 such that an intended operation is performed. Accordingly, even when it is described that the processor 210 performs certain operations, the processor 210 may control at least one component included in the data processing device 200 such that the certain operations are performed.

According to an embodiment, the processor 210 may obtain the face image of the object showing the teeth area. According to an embodiment, the face image of the object may be an image including the entire face of the object or a part of the face of the object. Also, the face image of the object showing the teeth area may be an image in which the teeth area is shown between lips of the object from the face of the object. Teeth are one of several features in an oral cavity, and are one of oral structures embedded in alveolar bones of an upper jaw and lower jaw.

According to an embodiment, the teeth area may denote an area including teeth or some of the teeth shown between the lips.

Hereinafter, for convenience of descriptions, the face image of the object showing the teeth area will be referred to as a first image.

According to an embodiment, the processor 210 may obtain the first image and replace the teeth area included in the first image with the virtual teeth area. The virtual teeth area may denote a future teeth area to be included in the oral cavity of the object when the oral cavity of the object is treated. In other words, the virtual teeth area may indicate how the present teeth area of the object included in the first image will change when oral treatment of the object is finished later. Hereinafter, for convenience of descriptions, the image in which the teeth area included in the first image is replaced with the virtual teeth area will be referred to as a second image.

According to an embodiment, the processor 210 may obtain, from the second image, an image including a face having a different attribute from the face included in the second image, by using a neural network trained to generate, from an input face image, a face image having a different attribute from the input face image. Hereinafter, for convenience of descriptions, an image output by the neural network when the second image is input to the neural network will be referred to as a third image.

According to an embodiment, the processor 210 may obtain the third image including the face having the different attribute from the face included in the second image, from the second image. According to an embodiment, the face having the different attribute may include at least one of a case where a pose of the face is changed, a case where a facial expression of the face is changed, a case where the shown teeth area is changed or a size of the shown teeth area is changed according to a degree the oral cavity is opened or an angle of the face, an age, and a case where a style, such as a hair color or hairstyle of the object, a makeup, or a skin one, is changed. The processor 210 may obtain the third image including a face different from the face included in the second image, in at least one of a pose, a facial expression, a face angle, a degree the teeth area is shown, an age, and a style, by using at least one neural network.

According to an embodiment, the neural network used by the processor 210 may be a deep neural network (DNN) for obtaining a face image in a multi-domain by changing an attribute of an input face image.

According to an embodiment, the DNN used by the processor 210 may include a star generative adversarial network (StarGAN).

According to an embodiment, the processor 210 may obtain the target virtual oral model from the 3D oral model obtained by scanning the oral cavity of the object. The 3D oral model may include 3D scan data of at least one of an upper jaw, a lower jaw, and occlusion in the oral cavity of the object.

According to an embodiment, the processor 210 may obtain, from the virtual oral model, an area corresponding to the teeth area included in the first image as the virtual teeth area.

According to an embodiment, the processor 210 may detect, from the first image, a lip line included in the face of the object, and identify an internal area of the lip line as the teeth area.

According to an embodiment, the processor 210 may obtain, from the virtual oral model, an area corresponding to an internal area of a lip line detected from the face image of the object as the virtual teeth area. The processor 210 may obtain the second image may replacing the inside of the lip line detected from the first image with the virtual teeth area.

According to an embodiment, the processor 210 may obtain a first feature point from the teeth area included in the first image, so as to replace the teeth area included in the first image with the virtual teeth area. The processor 210 may obtain a second feature point from the virtual oral model. The processor 210 may align the first feature point and the second feature point to replace the teeth area included in the first image with the virtual teeth area.

According to an embodiment, the processor 210 may automatically find the first feature point and the second feature point respectively from the teeth area included in the first image and the virtual oral model, and replace the teeth area included in the first image with the virtual teeth area.

Alternatively, according to an embodiment, the processor 210 may manually receive, from a user, selection of the first feature point and the second feature point respectively from the teeth area and the virtual oral model, and align the first feature point and the second feature point to replace the teeth area included in the first image with the virtual teeth area.

According to another embodiment, to obtain the second image, the processor 210 may use a virtual teeth template instead of the 3D oral model. In this regard, the processor 210 may use a face image of the object including a greater teeth area than the first image. According to an embodiment, the face image of the object including the greater teeth area than the first image may denote a case where a proportion of the teeth area occupying the face of the object is greater than a proportion of the teeth area to the face included in the first image. For example, the face image of the object including the greater teeth area than the first image may denote an image in which the face of the object further includes a teeth area not shown in the first image, together with the teeth area of the object shown in the first image. Hereinafter, for convenience of descriptions, the face image of the object including the greater teeth area than the first image will be referred to as an additional image.

The processor 210 may align the virtual teeth template in the greater teeth area included in the additional image. The processor 210 may align the virtual teeth template in a teeth area included in the additional image. The processor 210 may obtain, from the greater teeth area where the virtual teeth template is aligned, an area corresponding to the teeth area included in the first image as the virtual teeth area. The processor 210 may obtain the second image by replacing the teeth area included in the first image with the virtual teeth area.

The display 230 according to an embodiment may output the oral image on a screen.

When the display 230 is configured as a touch screen, the display 230 may be used as an input device, such as a user interface, as well as an output device. For example, the display 230 may include at least one of a liquid crystal display, a thin-film transistor-liquid crystal display, an organic light-emitting diode, a flexible display, a 3-dimensional (3D) display, and an electrophoretic display. There may be two or more displays 230, according to implementation.

According to an embodiment, the display 230 may output, on the screen, the face image of the object showing the teeth area, i.e., the first image.

According to an embodiment, the display 230 may output, on the screen, the 3D oral model obtained by scanning the oral cavity of the object. Also, according to an embodiment, the display 230 may output, on the screen, the target virtual oral model obtained from the 3D oral model.

According to an embodiment, the display 230 may output, on the screen, the second image in which the teeth area included in the first image is replaced with the virtual teeth area that is the area corresponding to the teeth area included in the first image, obtained based on the virtual oral model.

According to another embodiment, when the processor 210 uses the virtual teeth template to obtain the second image, the display 230 may output the face image of the object including the greater teeth area than the first image, i.e., the additional image, and the first image together on one screen, or output the additional image on a different screen from the first image.

According to an embodiment, the display 230 may output a teeth template on the screen. According to an embodiment, the display 230 may output, on the screen, a state in which a virtual template based on the teeth template is aligned on the greater teeth area included in the additional image. According to an embodiment, the display 230 may output, on the screen, the second image obtained as the teeth area included in the first image is replaced with the virtual teeth area obtained from the greater teeth area where the virtual teeth template is aligned.

According to an embodiment, the display 230 may output, on the screen, the third image including the face having the different attribute from the face included in the second image, the third image obtained through the neural network when the second image is input to the neural network.

According to an embodiment, the display 230 may output a user interface screen for a user input.

Figure 3:
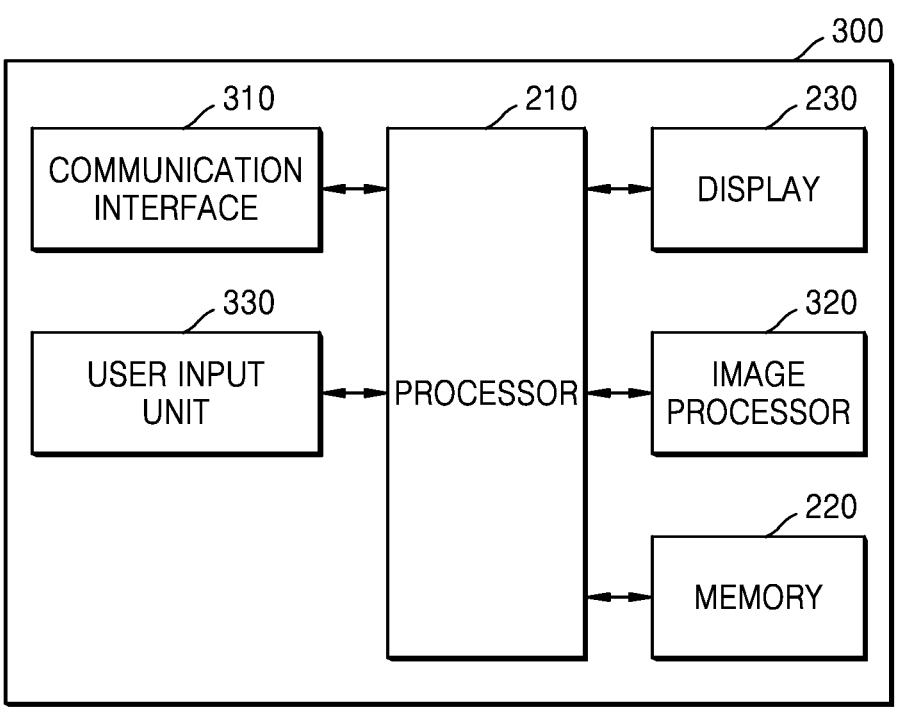
FIG. 3 is a diagram showing an example of the data processing device of FIG. 2.

FIG. 3 is a diagram showing an example of the data processing device of FIG. 2.

Referring to FIG. 3, a data processing device 300 may further include a communication interface 310, an image processor 320, and a user input unit 330, in addition to the processor 210, the memory 220, and the display 230.

The processor 210, the memory 220, and the display 230 included in the data processing device 300 of FIG. 3 perform same functions as the processor 210, the memory 220, and the display 230 included in the data processing device 200 of FIG. 2, and thus same reference numerals are used. Hereinafter, details overlapping those described with reference to the data processing device 200 of FIG. 2 will be omitted.

The user input unit 330 according to an embodiment may receive a user input for controlling the data processing device 300.

The user input unit 330 may include a touch panel for detecting a touch of a user, a button for receiving push manipulation of the user, and a user input device including a keyboard or a mouse for designating or selecting one point on a user interface screen, but is not limited thereto. Also, the user input unit 330 may include a voice recognition device for voice recognition. For example, the voice recognition device may be a microphone and may receive the user's voice command or voice request. Accordingly, the processor 210 may control an operation corresponding to the voice command or voice request to be performed.

According to an embodiment, the user input unit 330 may receive, from the user, such as a dentist, a user input requesting to obtain the second image in which the teeth area of the first image is replaced with the virtual teeth area.

According to an embodiment, the user input unit 330 may receive, from the user, a user input requesting to automatically or manually align the teeth area of the first image and the virtual teeth area.

According to an embodiment, the user input unit 330 may receive, from the user, a user input of receiving selections of feature points respectively from the teeth area and the virtual teeth area, so as to manually align the teeth area of the first image and the virtual teeth area.

According to an embodiment, when there are a plurality of teeth templates, the user input unit 330 may receive, from the user, a user input of receiving selection of one of the plurality of teeth templates.

According to an embodiment, the user input unit 330 may receive a user input of adjusting the selected teeth template according to an oral cavity of a patient.

According to an embodiment, the user input unit 330 may receive a user input of adjusting the selected teeth template as the target virtual teeth template.

According to an embodiment, the user input unit 330 may receive, from the user, the user input of requesting to obtain the third image including the face having the different attribute from the face included in the second image.

According to an embodiment, the user input unit 330 may receive, from the user, a user input of receiving selection of an image having which attribute the face included in the second image is to be converted to.

The image processor 320 according to an embodiment may perform operations for generating and/or processing an image.

According to an embodiment, the image processor 320 may generate the 3D oral model, based on the raw data received from the 3D scanner 100 and 110.

According to an embodiment, the image processor 320 may generate the target virtual oral model from the 3D oral model.

According to an embodiment, the image processor 320 may obtain, from the virtual oral model, the virtual teeth area that is the area corresponding to the teeth area included in the first image, and generate the second image in which the teeth area of the first image is replaced with the virtual teeth area.

According to an embodiment, the image processor 320 may generate an image in which the virtual teeth template is overlapped on the greater teeth area included in the additional image.

According to an embodiment, the image processor 320 may generate the second image in which the teeth area included in the first image is replaced with the virtual teeth area corresponding to the teeth area included in the first image, the virtual teeth area included in the additional image where the virtual teeth template is aligned.

The communication interface 310 according to an embodiment may communicate with at least one external electronic device through a wired or wireless communication network.

For example, the communication interface 310 may communicate with the 3D scanner 100 and 110 according to control by the processor 210. The communication interface 310 may receive the raw data from the 3D scanner 100 and 110 or obtain the 3D scan data. According to an embodiment, the communication interface 310 may obtain the 3D scan data by communicating with an external electronic device or an external server, other than the 3D scanner 100 and 110.

The communication interface 310 may include at least one short-range communication module performing communication according to the communication standard, such as Bluetooth, Wi-Fi, Bluetooth low energy (BLE), near field communication (NFC)/radio frequency identification (RFID), Wi-Fi direct (WFD), ultra-wideband (UWB), or ZigBee.

Also, the communication interface 310 may further include a long-range communication module performing communication with a server for supporting long-range communication according to the long-range communication standard. In particular, the communication interface 310 may include the long-range communication module performing communication through a network for Internet communication. For example, the communication interface 310 may include the long-range communication module performing communication through a communication network according to the communication standard, such as third generation (3G), fourth generation (4G), and/or fifth generation (5G).

Also, the communication interface 310 may communicate with the 3D scanner 100 and 110, external server, or external electronic device via wires. In this regard, the communication interface 310 may include at least one port to be connected to the 3D scanner 100 and 110 or external electronic device through a wired cable. The communication interface 310 may communicate with the 3D scanner 100 and 110 or external electronic device connected via wires through the at least one port.

According to an embodiment, the communication interface 310 may transmit, to the external electronic device or external server, the second image in which the teeth area included in the first image is replaced with the virtual teeth area.

According to an embodiment, the communication interface 310 may transmit, to the external electronic device or external server, the third image including the face having the different attribute from the face included in the second image, the third image obtained from the second image.

Figure 4:
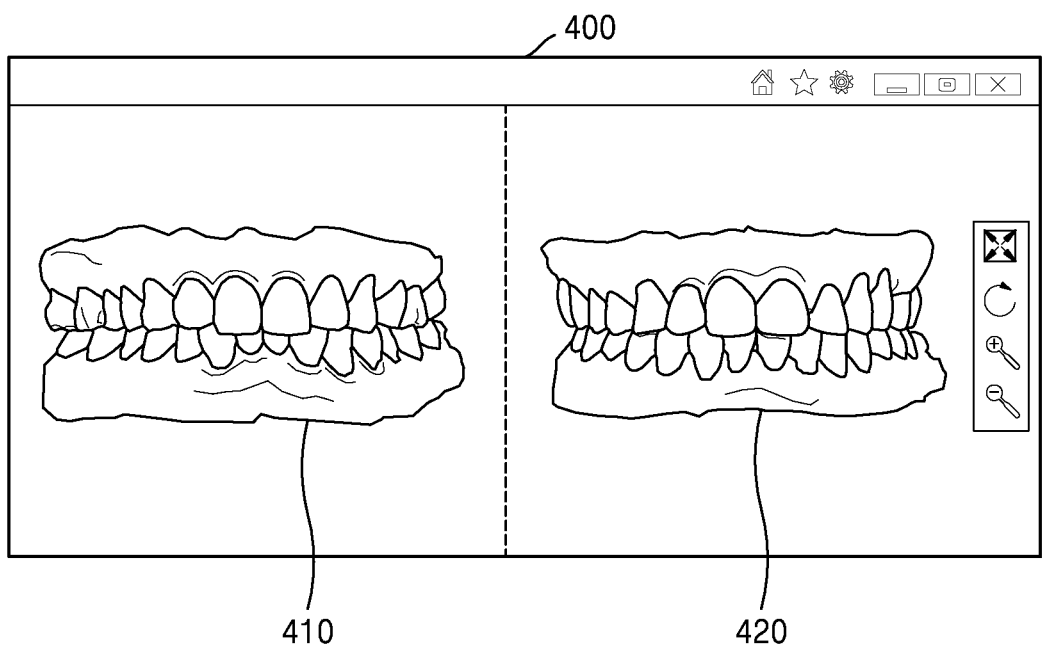
FIG. 4 is a diagram for describing a method by which a data processing device obtains a virtual oral model from a 3-dimensional (3D) oral model, according to an embodiment.

FIG. 4 is a diagram for describing a method by which a data processing device obtains a virtual oral model from a 3D oral model, according to an embodiment.

The data processing device may receive raw data from a 3D scanner and generate a 3D oral model by three-dimensionally modeling a structure of an oral cavity, based on the raw data. Alternatively, the data processing device may receive the 3D oral model from the 3D scanner. Alternatively, the data processing device may receive the 3D oral model from an external server or external device through a wired or wireless communication network.

The 3D oral model may also be referred to as 3D scan data. The 3D oral model may include the 3D scan data of a present oral cavity of an object, i.e., a patient. The 3D oral model may include the 3D scan data of at least one of an upper jaw, a lower jaw, and occlusion from among the oral cavity of the object.

Referring to FIG. 4, the data processing device may output, on a screen 400, a 3D oral model 410.

According to an embodiment, the data processing device may execute dedicated software for replacing the 3D oral model 410 with a target virtual oral model 420.

According to an embodiment, the data processing device may execute dedicated software for adjusting positions or shapes of teeth, thereby changing the 3D oral model 410 to an ideal shape. The data processing device may adjust the positions or shapes of the teeth included in the 3D oral model 410 automatically or manually according to a user input. For example, the data processing device may change the 3D oral model 410 by performing at least one of adjusting the position of the tooth included in the 3D oral model 410 in a left, right, up, or down direction, rotating the tooth, adjusting a size of the tooth, adjusting an interval between the teeth, rearranging the teeth by adjusting sizes of teeth left after some teeth are extracted, resetting a front of arch by setting a midline of at least one tooth from among an upper jaw, a lower jaw, and occlusion, and adjusting a color of the tooth.

Hereinafter, for convenience of descriptions, a model generated as the data processing device changes the 3D oral model 410 will be referred to as the virtual oral model 420. The virtual oral model 420 is generated from the 3D oral model 410 and may denote a future target virtual model when dental treatment is performed on the oral cavity of the patient.

According to an embodiment, the data processing device may adjust the positions, shapes, and arrangement states of the teeth according to information set by a user, and display simulations of states of the teeth before and after the adjustment together for comparison. For example, as shown in FIG. 4, the data processing device may output the 3D oral model 410 and the virtual oral model 420 together on one screen. Alternatively, the data processing device may output the 3D oral model 410 and the virtual oral model 420 on individual screens.

Figure 5:
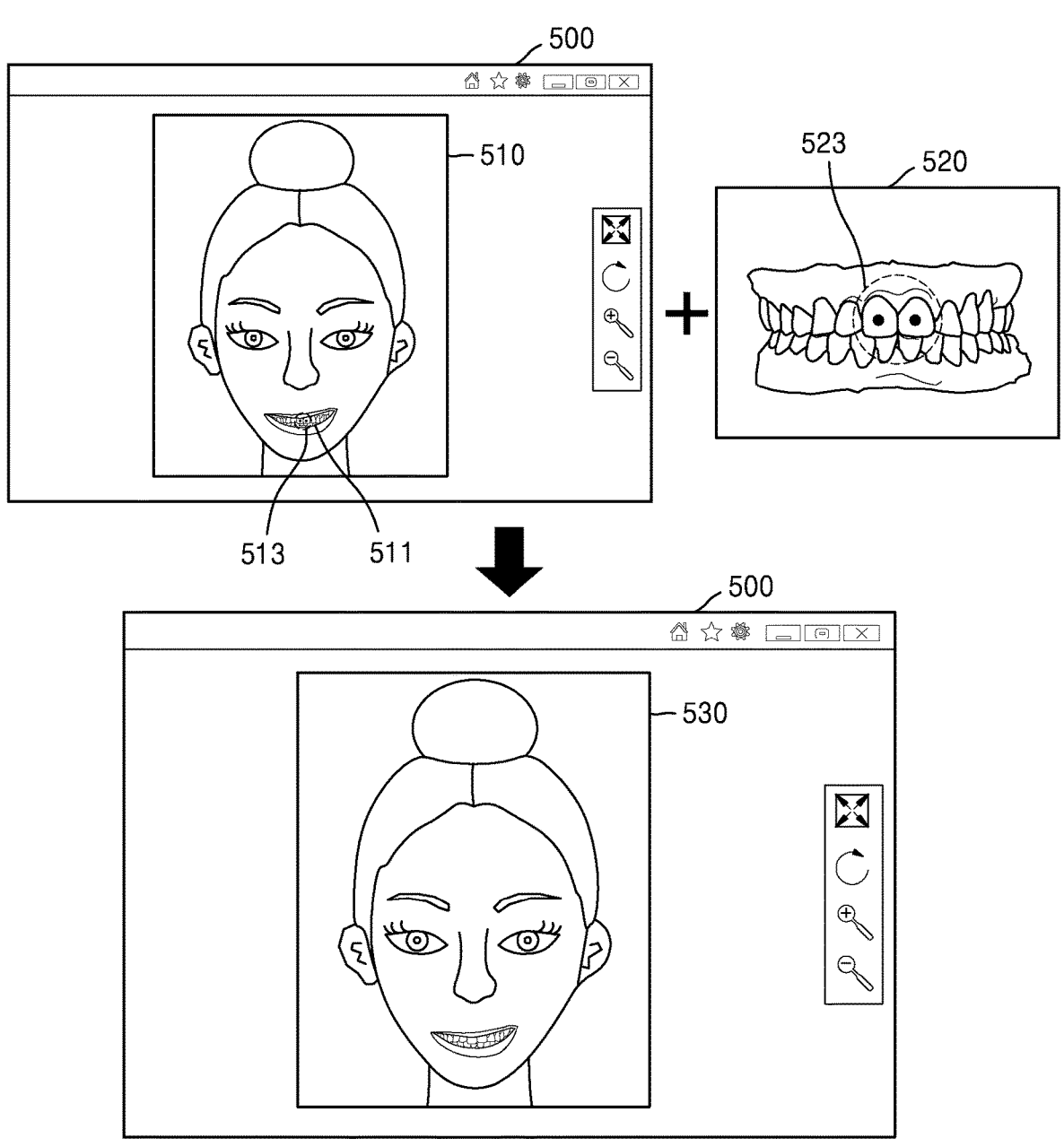
FIG. 5 is a diagram for describing a method by which a data processing device obtains a second image from a first image, according to an embodiment.

FIG. 5 is a diagram for describing a method by which a data processing device obtains a second image from a first image, according to an embodiment.

Referring to FIG. 5, the data processing device may obtain a first image 510. According to an embodiment, a first image may denote a face image of an object showing teeth.

A camera (not shown) mounted on the data processing device or connected to the data processing device through wired/wireless communication may obtain the first image 510 by photographing a face of the object showing the teeth. Alternatively, the data processing device may receive the first image 510 from an external server or computing device through a communication network. Alternatively, the data processing device may receive the first image 510 from an external electronic device or external storage medium through a universal serial bus (USB) or a high-definition multimedia interface (HDMI) cable.

The data processing device may output the first image 510 on a screen 500 of the data processing device.

According to an embodiment, the data processing device may detect a teeth area 511 from the first image 510. The teeth area 511 is an area including the teeth of the object in the first image 510, and may denote an area including all or some of the teeth shown between lips of the object. A position or area of the teeth area 511 shown may vary depending on a facial expression or pose of the object, or a degree the object opens his/her oral cavity.

According to an embodiment, the data processing device may obtain a 3D oral model that is scan data of the present oral cavity of the object. Also, the data processing device may obtain a virtual oral model 520 from the 3D oral model according to the method described with reference to FIG. 4.

According to an embodiment, the data processing device may obtain, from the virtual oral model 520, an area overlapping the teeth area 511 detected from the first image 510.

Hereinafter, the area included in the virtual oral model 520, which overlaps the teeth area 511 of the first image 510, will be referred to as a virtual teeth area. As described above, the virtual teeth area is a future teeth area to be included in the oral cavity of the object, and may show how the teeth area 511 of the object included in the first image 510 will look like when oral treatment of the object is done in the future.

According to an embodiment, the data processing device may obtain the virtual teeth area corresponding to the teeth area 511 from the virtual oral model 520 by using reference data. The reference data may denote surface data of the object obtained through a scan. The reference data may be used to align areas matching each other in images.

According to an embodiment, the data processing device may automatically obtain a second image 530 by obtaining, from the virtual oral model 520, the virtual teeth area overlapping the teeth area 511 of the first image 510, and aligning the virtual teeth area with the teeth area 511 of the first image 510.

For example, the data processing device may execute dedicated software for replacing a teeth area included in an image with a virtual teeth area to replace the teeth area 511 included in the first image 510 with the virtual teeth area.

The data processing device may automatically replace the teeth area 511 with the virtual teeth area by detecting feature points matching in the teeth area 511 of the first image 510 and the virtual oral model 520, and aligning the detected feature points. Alternatively, the data processing device may automatically replace the teeth area 511 with the virtual teeth area by detecting a lip line from the first image 510, detecting feature points from an internal area of the detected lip line, detecting matching feature points from the virtual oral model 520, which match the feature points detected from the inside of the lip line, and aligning the feature points.

Alternatively, according to an embodiment, the data processing device may manually align the virtual teeth area with the teeth area 511 of the first image 510. For example, a user may select a position of a first feature point 513 from the teeth area 511 of the first image 510 output from the data processing device, and select a position of a second feature point 523 from the virtual oral model 520. The data processing device may replace the teeth area 511 in the first image 510 with the virtual teeth area by matching and aligning the first feature point 513 and the second feature point 523 at a position selected by the user.

The data processing device may output the second image 530 on the screen 500. Referring to FIG. 5, the second image 530 includes the same face image of the object as the first image 510, but a teeth portion of the object is different from the first image 510. In other words, in the second image 530, the teeth area 511 is replaced with the virtual teeth area obtained from the virtual oral model 520.

As such, according to an embodiment, the data processing device may generate the second image 530 by obtaining the virtual teeth area from the virtual oral model 520 obtained from the 3D oral model, and aligning the virtual teeth area with the teeth area 511 of the first image 510. The object, i.e., the patient, may easily check how virtual teeth will look like on his/her face when the oral treatment is finished, by using the second image 530.

Figure 6:
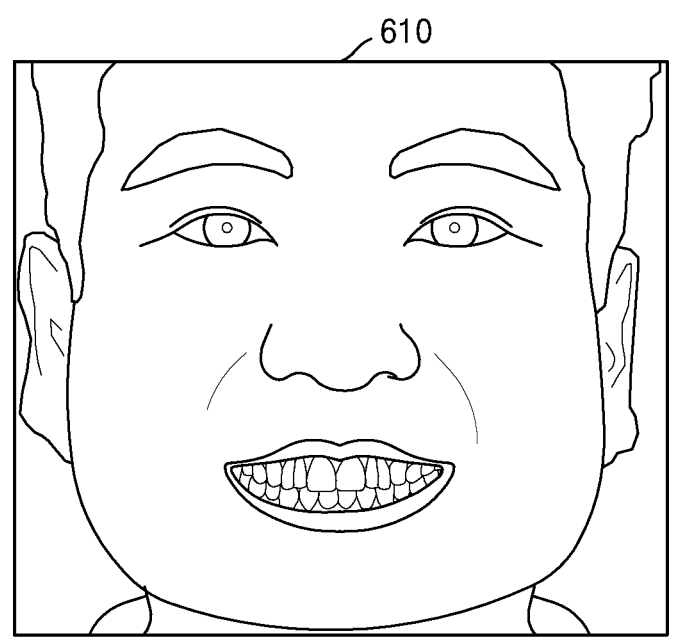
FIGS. 6 and 7 are diagrams for describing a method by which a data processing device obtains a second image from a first image, according to other embodiments.
Figure 6:
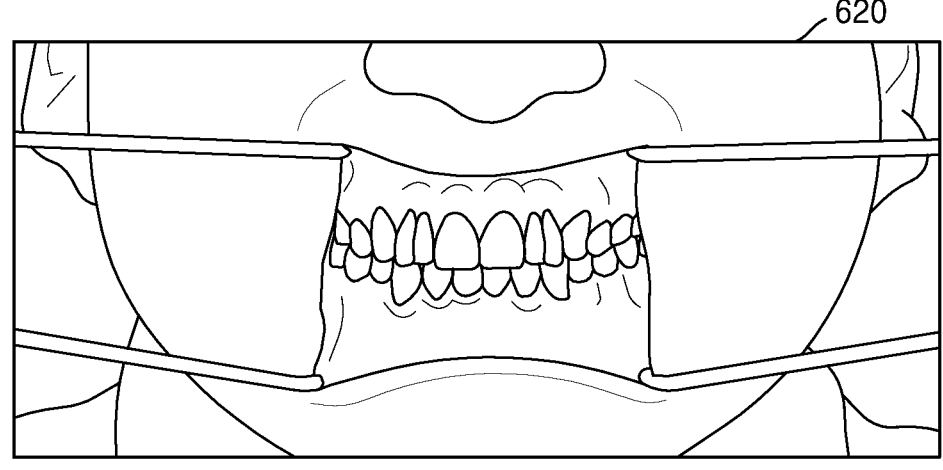
Figure 7:
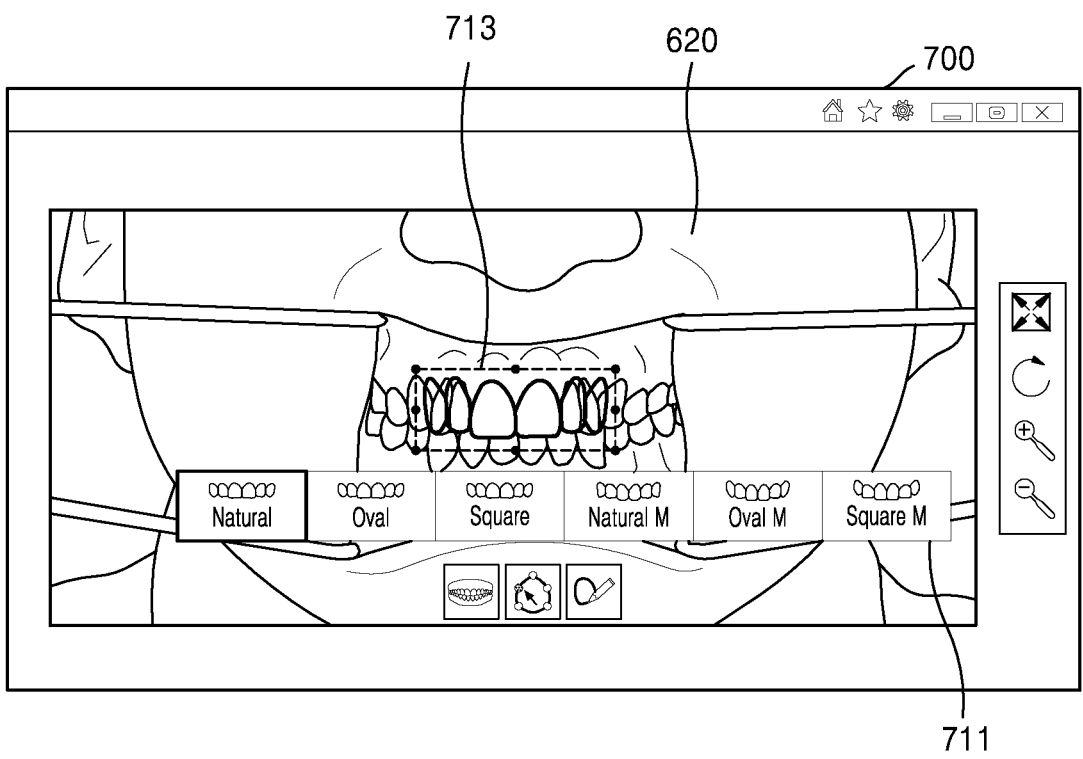
Figure 7:
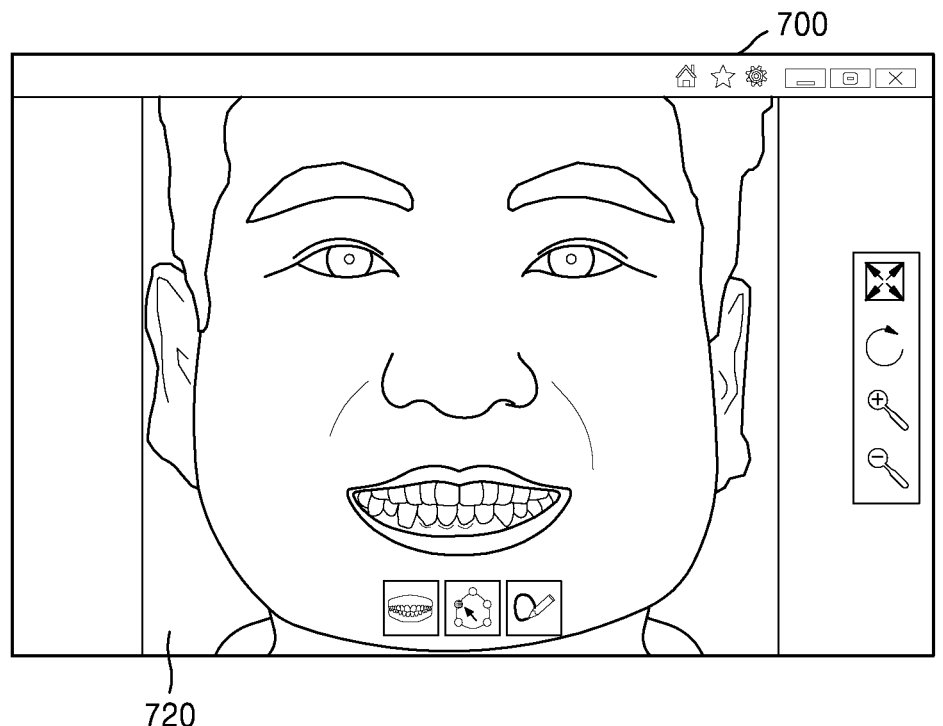

FIGS. 6 and 7 are diagrams for describing a method by which a data processing device obtains a second image from a first image, according to other embodiments.

Referring to FIG. 6, the data processing device may obtain a first image 610. The first image 610 may denote a face image of an object showing a teeth area.

According to an embodiment, the data processing device may further obtain an additional image 620 in addition to the first image 610. The additional image 620 may denote an image of a same object as the object included in the first image 610, but showing more teeth of the object than the first image 610. In other words, the additional image 620 may be an image including the teeth area included in the first image 610, and further including a teeth area that is not included in the teeth area included in the first image 610. Also, the additional image 620 may be an image obtained as the object is photographed at a same angle as the first image 610 or an image obtained as the object is photographed within a certain angle difference from the first image 610.

The data processing device may obtain the first image 610 and the second image, i.e., the additional image 620, where more teeth of the object are shown than the first image 610, through a camera or the like mounted on the data processing device or connected to the data processing device through wired/wireless communication. Alternatively, the data processing device may receive the first image 610 and/or the second image 620 from an external server or computing device through a communication network, or receive the first image 610 and/or the second image 620 from an external electronic device or external storage medium through a USB or HDMI cable.

According to an embodiment, the data processing device may execute software for replacing a teeth area included in an image with a virtual teeth template.

Referring to FIG. 7, the data processing device may output, on a screen 700 of the data processing device, the additional image 620 shown in FIG. 6.

Also, the data processing device may output, on screen 700, a teeth template 711 in various forms, stored in a memory or the like. The teeth template 711 may denote information indicating arrangement states of teeth having various shapes or sizes.

As shown in FIG. 7, the teeth template 711 may include various types of templates. For example, the teeth template 711 may include templates of a natural type, an oval type, a square type, a natural M type, an oval M type, and a square M type, according to shapes and arrangement states of the teeth. However, this is only an embodiment, and the teeth template 711 may further include another type of template that is not described above, or may include only some of the above-described templates.

A user may select one of a plurality of templates included in the teeth template 711 by using the data processing device. Alternatively, the data processing device may automatically select a template having highest similarity with the teeth area of the object included in the additional image 620, from among the plurality of templates included in the teeth template 711. The data processing device may align the selected template on the teeth area included in the additional image 620.

The data processing device may additionally adjust the template aligned on the teeth area included in the additional image 620 according to a user input or automatically. For example, the data processing device may adjust, according to the user input or automatically, at least one of a shape, size, position, and angle of a tooth included in the template, an interval between teeth, arrangement states of a plurality of teeth, a front of arch, and a material or color of a tooth. The material of the tooth may be information indicating, for example, whether the tooth will be in ceramic or gold. The color of the tooth may include information indicating a whitening degree of the tooth, for example, chroma, brightness, transparency, and shadow of the tooth.

The data processing device may obtain a virtual teeth template by adjusting the template according to the teeth area of the object included in the additional image 620 while adjusting the template according to a target oral shape when an oral cavity of the object is treated.

Hereinafter, a teeth template having a target ideal shape, obtained from the selected teeth template, will be referred to as the virtual teeth template. The virtual teeth template may be model data indicating a case where teeth, teeth arrangements, teeth colors, and the like have target forms. The virtual teeth template may be obtained by adjusting the selected teeth template or may be the same as the selected teeth template.

Referring to FIG. 7, the data processing device may output, on the screen 700, a state in which a virtual teeth template 713 is aligned on the additional image 620. In other words, the data processing device may output, on the screen 700, a state in which a greater teeth area included in the additional image 620 is replaced with the virtual teeth template 713.

The data processing device may obtain, as a virtual teeth area, an area corresponding to the teeth area included in the first image 610, from the teeth area in the additional image 620, which is replaced with the virtual teeth template 713. The virtual teeth area may denote an area suiting the size or position of the teeth area included in the first image 610, from among the teeth area in the additional image 620, which is replaced with the virtual teeth template 713. When sizes of the additional image 620 and the first image 610 are different from each other, the virtual teeth area may be obtained considering a size difference between the additional image 620 and the first image 610.

The data processing device may obtain a second image 720 by replacing the teeth area included in the first image 610 with the virtual teeth area. The data processing device may output the second image 720 on the screen 700.

As shown in FIG. 7, the second image 720 relates to the same face image of the object as the first image 610, but a teeth portion of the object is different from the first image 610. This is because the teeth area included in the second image 720 has been replaced with the virtual teeth area obtained from the virtual teeth template 713 aligned on the greater teeth area of the additional image 620.

As such, according to an embodiment, the data processing device may replace the greater teeth area included in the additional image 620 with the target virtual teeth template 713. Also, according to an embodiment, the data processing device may obtain the second image 720 by obtaining the virtual teeth area corresponding to the teeth area of the first image 610 from the teeth area of the additional image 620 replaced with the virtual teeth template 713, and replacing the teeth area included in the first image 610 with the virtual teeth area.

Figure 8:
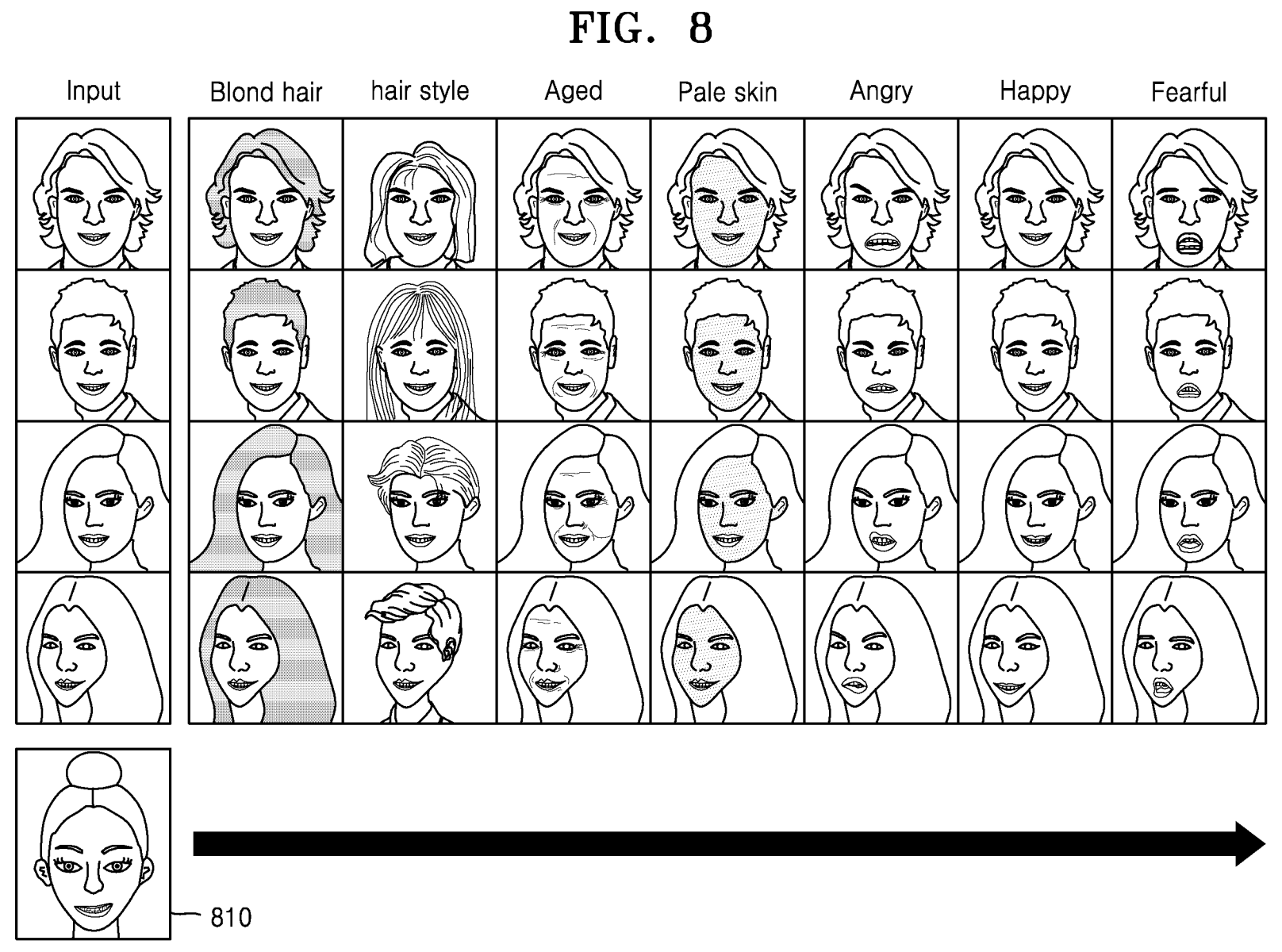

FIG. 8 is a diagram for describing face images having different attributes being obtained from a face image input through a neural network, according to an embodiment.

Referring to FIG. 8, images indicated by "Input" at the leftmost are original images, and images indicated in a 4×7 matrix at the right of the original images are output images. FIG. 8 illustrates the original images being input in two domains. In other words, in FIG. 8, the original images may be changed to a domain of blond hair, hair style, aged, and pale skin, and a domain of angry, happy, and fearful, through a neural network.

FIG. 8 illustrates results output as a single model simultaneously learns two data sets. However, a domain may change according to a learned data set, and the more the learned data sets, the more the domains.

According to an embodiment, a data processing device may input a second image 810 into the neural network. In this case, like the images shown in the 4×7 matrix of FIG. 8, a face of an object included in the second image 810 may be output in forms of styles having blond hair different from an original hair color, having a different hair style, having an aged face, or having a changed face color. Also, the face of the object included in the second image 810 may be changed to images having different facial expressions from an original face, for example, different attributes, such as an angry face, a happy face, and a fearful face.

Figure 9:
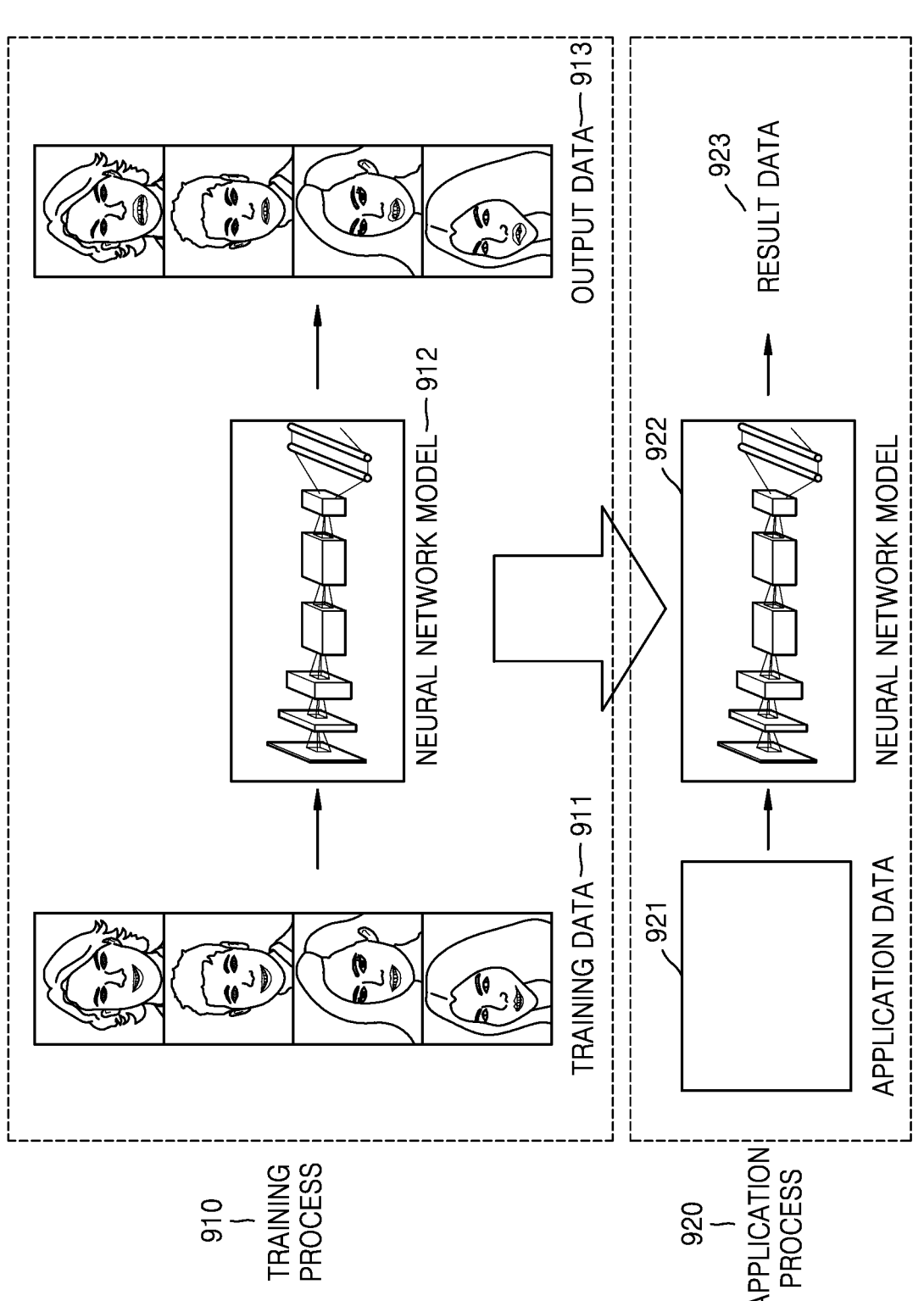
FIG. 9 is a diagram for describing a neural network trained to generate, from an input face image, face images having attributes different from the input face image, according to an embodiment.

FIG. 9 is a diagram for describing a neural network trained to generate, from an input face image, face images having attributes different from the input face image, according to an embodiment.

Referring to FIG. 9, a process of generating a face image having a different attribute from an input face image by using artificial intelligence may largely include two processes.

First, during a training process 910, a neural network, i.e., a neural network model 912, may be trained by using a plurality of pieces of training data 911 as inputs. Output data 913 that is a training result may be fed back to the neural network model 912 again to be used to update a weight value of the neural network model 912.

In response to the plurality of pieces of training data 911 being input, the neural network model 912 may learn and/or train a method of detecting data having a different attribute from the plurality of pieces of training data 911, and generate the output data, based on a learning and/or training result.

In detail, the training data 911 may include a plurality of face images. The plurality of face images may include at least one of face images with various poses or facial expressions, images in which degrees a teeth area is shown are different, and images in which styles vary, for example, hair styles or degrees of makeup, and skin colors.

The neural network model 912 may include a plurality of neural network layers. Each of the plurality of neural network layers includes a plurality of weight values, and performs a neural network arithmetic operation via an arithmetic operation between an arithmetic operation result of a previous layer and the plurality of weight values.

The plurality of weight values in each of the neural network layers may be optimized by a result of training an AI model. For example, the plurality of weight values may be updated to reduce or minimize a loss value or a cost value obtained by the AI model during the training process 910. An artificial neural network may include a DNN and may be, for example, a convolutional neural network (CNN), a DNN, a recurrent neural network (RNN), a restricted Boltzmann machine (RBM), a deep belief network (DBN), a bidirectional recurrent DNN (BRDNN), or deep Q-networks (DQN), but is not limited thereto.

The neural network model 912 may include a mapping network. The mapping network is nonlinear and reduce a biased correlation between features. The mapping network may include a plurality of layers. Each layer may be represented by at least one node, and nodes between layers may be connected by an edge. The nodes may be fully connected to the nodes included in the previous and subsequent layers.

The neural network model 912 may obtain an intermediate vector by passing input information through the mapping network. The intermediate vector may be a weight containing attribute information of different styles. For example, when a feature vector extracted from the attribute information relates to a feature corresponding to an angry facial expression, the neural network model 912 may generate an intermediate vector having such a feature. For example, when the feature vector extracted from the attribute information relates to a feature corresponding to an attribute related to a hair style, the neural network model 912 may generate an intermediate vector having a feature of the hair style.

The neural network model 912 may synthesize an image by applying the style information for each of the plurality of layers, by using the generated intermediate vector. The neural network model 912 may receive an input of a tensor. The tensor may be a data structure containing information of a deep learning model. The tensor is a base image to which styles of pieces of training data are not reflected, and may be information representing an average image. According to an embodiment, the tensor may denote a layout of an additional information area having a basic style.

The neural network model 912 may include a plurality of layers starting from 4×4×512 tensors to 1024×1024×3 tensors. Each layer may be connected to a next layer through convolution and upsampling.

A weight may be input to each layer of the neural network model 912. The neural network model 912 may be trained to represent an attribute or style of each layer by using the intermediate vector, i.e., the weight.

When a depth of the layer is shallow, a low level feature, i.e., a coarse feature, of an image may be extracted, and when the depth of the layer is deep, a detailed high level feature may be extracted.

The neural network model 912 may obtain a result image, based on features obtained from a low level to a high level. The result image may be an image on a different domain.

Each training result may be indicated as the output data 913 in the neural network model 912. The output data 913 may be a face image having a different attribute from an input face image. The output data 913 may be used to update the weight values of the neural network model 912. When the neural network model 912 is trained such that the training result exceeds certain reliability, such a model may be used as a trained neural network model 922.

During an application process 920, application data 921 may be input to the trained neural network model 922 to obtain, from the input application data 921, result data 923 having a different attribute from the input application data 921.

According to an embodiment, the application data 921 may be a second image in which a teeth area of a first image is replaced with a virtual teeth area, and the result data 923 output from the neural network model 922 may be a third image including a face having a different attribute from a face included in the second image.

According to an embodiment, the neural network model 912 may be a generative adversarial network (GAN). In detail, the neural network model 912 may be a StarGAN. The StarGAN is an image conversion model that changes an attribute of a provided image from one domain to another domain. The attribute may denote meaningful features in the image. For example, the attribute may include a facial expression or face pose, a face angle according to the face pose, a degree teeth are shown, an age, a face color, a hair color, or a hair style. The domain may indicate a set of images sharing an attribute value. For example, an angry facial expression and a blond hair color may configure different domains.

The neural network model 912 may receive, as input values, domain information to be changed and an original image, i.e., the second image. The StarGAN may learn mapping between all available domains through one generator. For example, the StarGAN may receive an image and domain information as the training data 911 and learn to flexibly change an image to a suitable domain. The StarGAN may use a form, such as binary or one-hot vector to represent such domain information. The StarGAN may be trained to randomly generate a target domain label while learning the neural network model 912, and flexibly change an image to a target domain. Accordingly, a domain label may be controlled and an image may be changed to a desired domain.

The StarGAN is jointly trainable by adding a mask vector to the domain label. In other words, the StarGAN may ignore a label unknown to the neural network model 912 and focus on labels of a certain data set. In this regard, the neural network model 912 may satisfactorily perform a task, such as a facial expression synthesis.

An operation of learning a method of obtaining an image having a different attribute from an image by using the neural network model 912 may be performed by a data processing device. Alternatively, such a learning operation may be performed by an external computing device separate from the data processing device. For example, the operation of learning the method of obtaining an image having a different attribute from an image by using the neural network model 912 may require relatively complicated throughput. Accordingly, the external computing device may perform the learning operation and the data processing device may receive the neural network model 912 that has been trained from the external computing device, thereby reducing the throughput to be processed by the data processing device. The data processing device may receive the neural network model 912 from an external server and store the same in a memory, and obtain an image having a different attribute from an image by using the stored neural network model 912.

Figure 10:
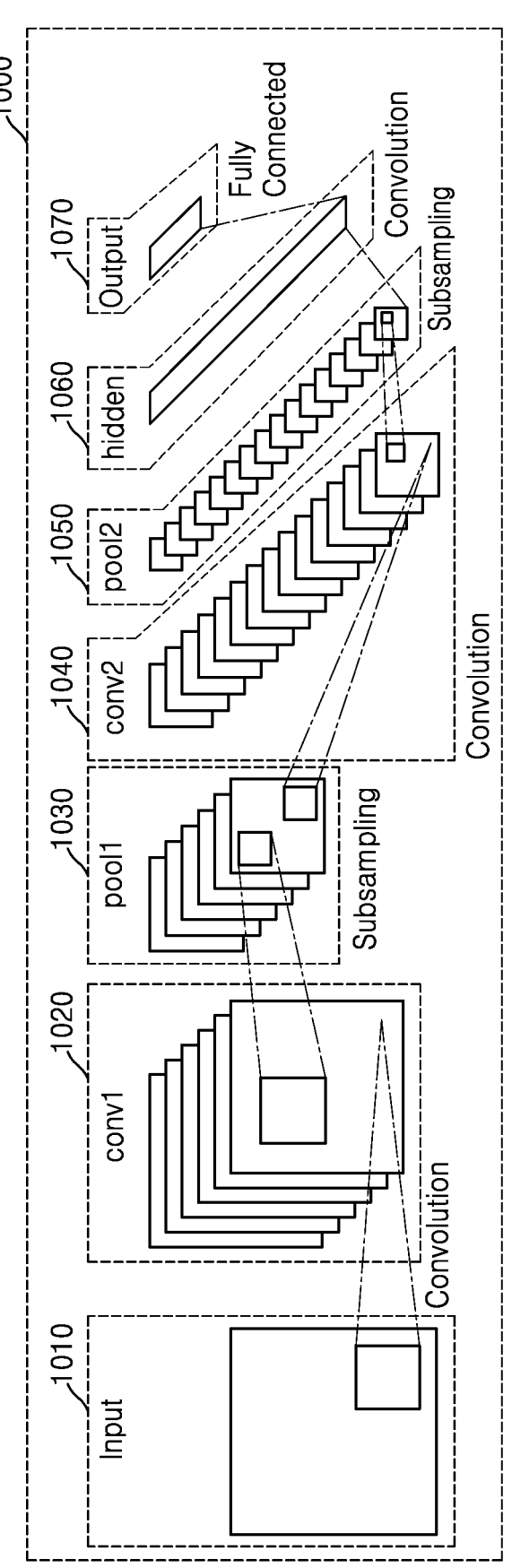
FIG. 10 illustrates a convolutional neural network (CNN)-based neural network, according to an embodiment.

FIG. 10 illustrates a CNN-based neural network, according to an embodiment.

In detail, FIG. 10 illustrates a deep CNN (DCNN) having a plurality of depths by including a plurality of layers. A data processing device may obtain a third image from a second image through a CNN-based neural network 1000.

According to an embodiment, the second image may be input to an input layer 1010 of the CNN-based neural network 1000. In the CNN-based neural network 1000, a convolution layer and a pooling layer are alternately arranged, and depths of filter layers increase from left to right. Also, a final end of the CNN-based neural network 1000 may be a fully connected layer.

The convolution layer is a layer of pieces of data generated according to a convolution operation, and the pooling layer is a layer for reducing the number or sizes of pieces of data through an operation called subsampling or pooling. Through the convolution layer and the pooling layer, pieces of data indicating features of an input frame are generated. Also, the pieces of data generated through the convolution layer and the pooling layer are transmitted to a hidden layer formed as a fully connected layer, and thus result data of an object recognized from features may be output.

For example, the CNN-based neural network 1000 may include the input layer 1010, a first convolution layer 1020, a first pooling layer 1030, a second convolution layer 1040, a second pooling layer 1050, a hidden layer 1060, and an output layer 1070. Here, depths of a convolution layer and pooling layer may vary, and a depth of a hidden layer may also vary. Also, the deeper the depths of the convolution layer and pooling layer, the more accurate the output data. This is because the deeper the depths of the convolution layer and pooling layer, the more specific the pieces of information indicating features of an input image, and thus an object recognized from the features may be more accurately recognized. Also, a depth and form of the neural network may be variously designed considering accuracy of a result, reliability of a result, and an operation processing speed and capacity of a processor.

Figure 11:
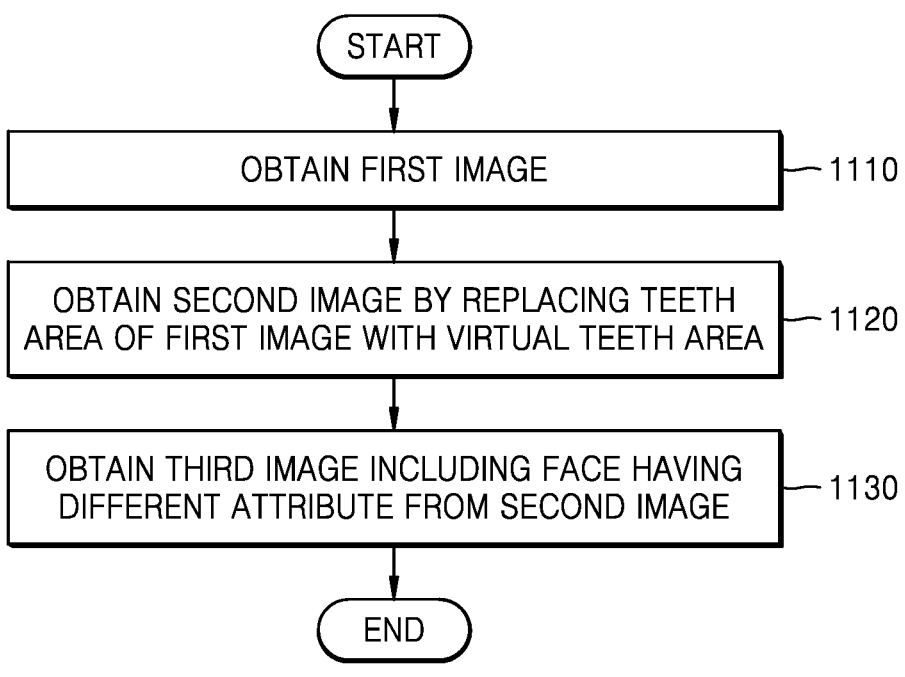
FIG. 11 is a flowchart of an oral image processing method according to an embodiment.

FIG. 11 is a flowchart of an oral image processing method according to an embodiment.

Referring to FIG. 11, a data processing device may obtain a first image (operation 1110). The first image may include a face image of an object showing a teeth area.

The data processing device may replace the teeth area included in the first image with a virtual teeth area (operation 1120).

According to an embodiment, the data processing device may use a 3D scan data, i.e., a 3D oral model, so as to replace the teeth area included in the first image with the virtual teeth area. The data processing device may obtain the 3D oral model of an oral cavity of the object, and obtain a target virtual oral model from the 3D oral model. The data processing device may obtain, from the virtual oral model, an area overlapping the teeth area included in the first image as the virtual teeth area.

According to another embodiment, the data processing device may use a teeth template to replace the teeth area included in the first image with the virtual teeth area. Also, the data processing device may further use an additional image together with the first image. The additional image may denote a face image of the object including a greater teeth area than the teeth area of the object of the first image. The data processing device may align a virtual teeth template in the greater teeth area included in the additional image. The virtual teeth template may denote a target teeth template of teeth of the object, obtained from a teeth template stored in the data processing device. The data processing device may replace the teeth area of the additional image with the virtual teeth template and obtain, as the virtual teeth area, an area corresponding to the teeth area included in the first image therefrom. The data processing device may obtain a second image by replacing the teeth area included in the first image with the virtual teeth area.

The data processing device may obtain a third image including a face having a different attribute from the second image (operation 1130). The data processing device may obtain, from the second image, the third image including the face having the different attribute from the face included in the second image, by using a neural network trained to generate, from an input face image, a face image having a different attribute from the input face image.

The face having the different attribute from the face included in the second image may be a face different from the face included in the second image in at least one of styles, such as a pose, a facial expression, a degree a teeth area is shown, a skin color, a hair style, and makeup.

The neural network used by the data processing device may be a DNN for obtaining a face image in a multi-domain by changing an attribute of an input face image. Also, the DNN may be a StarGAN.

An oral image processing method according to an embodiment of the present disclosure may be recorded on a computer-readable recording medium by being implemented in a form of program commands executed by using various computers. Also, an embodiment of the present disclosure may include a computer-readable storage medium having recorded thereon at least one program including at least one instruction for executing the oral image processing method.

The oral image processing method according to an embodiment of the present disclosure may be implemented by a computer program product including a computer-readable recording medium having recorded thereon a program for executing the oral image processing method including obtaining, as a first image, a face image of an object showing a teeth area, obtaining a second image by replacing the teeth area included in the first image with a virtual teeth area, and obtaining, from the second image, a third image including a face having a different attribute from a face included in the second image, by using a neural network trained to generate, from an input face image, a face image having a different attribute from the input face image.

The computer-readable recording medium may include at least one of a program command, a data file, or a data structure. Examples of the computer-readable recording medium include magnetic media such as hard disks, floppy disks, and magnetic tapes, optical media such as CD-ROMs and DVDs, magneto-optical media such as floptical disks, and hardware devices configured to store and perform program commands, such as read-only memory (ROM), random-access memory (RAM), and flash memory.

A machine-readable storage medium may be provided in the form of a non-transitory storage medium. The "non-transitory storage medium" may denote that a storage medium is a tangible device. The "non-transitory storage medium" may include a buffer where data is temporarily stored.

According to an embodiment, a data processing method according to various embodiments in the present specification may be provided by being included in a computer program product. The computer program product may be distributed in the form of the machine-readable storage medium (e.g., a compact disc read-only memory (CD-ROM). Alternatively, the computer program product may be distributed (e.g., downloaded or uploaded) directly or online through an application store (e.g., PlayStore™) or between two user devices (e.g., smartphones). In detail, the computer program product according to an embodiment may include a storage medium having recorded thereon a program including at least one instruction for executing the data processing method according to an embodiment.

While the embodiments have been particularly shown and described in detail, it will be understood by one of ordinary skill in the art that various changes in form and details may be made therein without departing from the spirit and scope of the present disclosure as defined by the following claims.

The invention claimed is:

1. An oral image processing method comprising:
obtaining, as a first image, a face image of an object showing a teeth area;
obtaining, as an additional image, a face image of the same object captured in the same direction as the first image and including a greater teeth area than the first image, the greater teeth area including the teeth area shown in the first image and an additional teeth area not shown in the first image;
replacing the greater teeth area included in the additional image with a virtual teeth template to generate a modified additional image;
obtaining, as a virtual teeth area, a region corresponding to the teeth area included in the first image from the modified additional image;
obtaining a second image by replacing the teeth area included in the first image with the virtual teeth area, the virtual teeth area being a two-dimensional image region; and
using a neural network trained to learn images with different visible teeth and to generate a face image having a different teeth area from an input face image, obtaining, from the second image, a third image including a face having a different position or size of a visible teeth area compared to a face included in the second image.

2. The oral image processing method of claim 1, wherein the neural network is a deep neural network (DNN) for obtaining a face image from a multi-domain by converting an attribute of the input face image, wherein the DNN includes a star generative adversarial network (StarGAN).

3. The oral image processing method of claim 1, further comprising detecting a lip line included in the face image of the object included in the first image,
wherein the teeth area comprises an internal area of the detected lip line, and
the virtual teeth area comprises an area corresponding to the internal area of the detected lip line from the modified additional image.

4. The oral image processing method of claim 1, wherein the obtaining of the second image comprises:
obtaining a first feature point from the teeth area included in the first image;
obtaining a second feature point from the modified additional image; and
aligning the first feature point and the second feature point.

5. The oral image processing method of claim 4, wherein the obtaining of the second image further comprises receiving, from a user, selection on the first feature point and the second feature point from each of the teeth area and the modified additional image.

6. An oral image processing apparatus comprising a processor configured to execute at least one instruction, wherein the processor is configured to execute the at least one instruction to:

obtain, as a first image, a face image of an object showing a teeth area;

obtain, as an additional image, a face image of the same object captured in the same direction as the first image and including a greater teeth area than the first image, the greater teeth area including the teeth area shown in the first image and an additional teeth area not shown in the first image;

replace the greater teeth area included in the additional image with a virtual teeth template to generate a modified additional image;

obtain, as a virtual teeth area, a region corresponding to the teeth area included in the first image from the modified additional image;

obtain a second image by replacing the teeth area included in the first image with the virtual teeth area, the virtual teeth area being a two-dimensional image region; and using a neural network trained to learn images with different visible teeth and to generate a face image having a different teeth area from an input face image, obtain, from the second image, a third image including a face having a different position or size of a visible teeth area compared to a face included in the second image.

7. A non-transitory computer-readable recording medium having recorded thereon a program for implementing an oral image processing method comprising:

obtaining, as a first image, a face image of an object showing a teeth area;

obtaining, as an additional image, a face image of the same object captured in the same direction as the first image and including a greater teeth area than the first image, the greater teeth area including the teeth area shown in the first image and an additional teeth area not shown in the first image;

replacing the greater teeth area included in the additional image with a virtual teeth template to generate a modified additional image;

obtaining, as a virtual teeth area, a region corresponding to the teeth area included in the first image from the modified additional image;

obtaining a second image by replacing the teeth area included in the first image with the virtual teeth area, the virtual teeth area being a two-dimensional image region; and using a neural network trained to learn images with different visible teeth and to generate a face image having a different teeth area from an input face image, obtaining, from the second image, a third image including a face having a different position or size of a visible teeth area compared to a face included in the second image.

* * * * *